United States Patent
Blacker

(10) Patent No.: US 11,229,490 B2
(45) Date of Patent: Jan. 25, 2022

(54) SYSTEM AND METHOD FOR MONITORING OF GUIDE CATHETER SEATING

(71) Applicant: Corindus, Inc., Waltham, MA (US)

(72) Inventor: Steven J. Blacker, Framingham, MA (US)

(73) Assignee: Corindus, Inc., Waltham, MA (US)

( * ) Notice: Subject to any disclaimer, the term of this patent is extended or adjusted under 35 U.S.C. 154(b) by 1018 days.

(21) Appl. No.: 14/315,025

(22) Filed: Jun. 25, 2014

(65) Prior Publication Data

US 2015/0005738 A1 Jan. 1, 2015

Related U.S. Application Data

(60) Provisional application No. 61/864,808, filed on Aug. 12, 2013, provisional application No. 61/839,459, filed on Jun. 26, 2013.

(51) Int. Cl.
*A61B 34/30* (2016.01)
*A61B 34/20* (2016.01)
(Continued)

(52) U.S. Cl.
CPC .............. *A61B 34/30* (2016.02); *A61B 34/20* (2016.02); *A61B 2034/301* (2016.02);
(Continued)

(58) Field of Classification Search
CPC .. A61M 25/0105–2025/0166; A61M 2205/10; A61M 2205/103; A61M 2205/106; A61M 2205/33; A61M 2205/3303; A61M 2205/3306; A61B 34/30; A61B 34/32; A61B 2034/2055; A61B 2034/2057; A61B 2034/301;
(Continued)

(56) References Cited

U.S. PATENT DOCUMENTS 5,246,007 A * 9/1993 Frisbie ..................... A61B 8/12
600/465
5,334,294 A 8/1994 Iwai et al.
(Continued)

FOREIGN PATENT DOCUMENTS

EP 1421913 5/2004
EP 2322088 5/2011

OTHER PUBLICATIONS

The Free Dictionary.com. "Guide catheter". https://medical-dictionary.thefreedictionary.com/guide+catheter. Accessed Sep. 24, 2019. (Year: 2019).*

(Continued)

*Primary Examiner* — Bhisma Mehta
*Assistant Examiner* — Larry R. Wilson

(57) ABSTRACT

A method for monitoring the seating of a guide catheter during a catheter procedure includes monitoring at least one parameter of the catheter procedure and determining if the at least one parameter indicates that a guide catheter is out of position. If the at least one parameter indicates the guide catheter is out of position, an alert is displayed and the position of the guide catheter is adjusted. The parameter may be, for example, blood pressure, an ST wave of an electrocardiogram, contrast agent, fluoroscopic images of a region including the distal end of the guide catheter and ultrasound signals.

14 Claims, 4 Drawing Sheets

(51) Int. Cl.
*A61M 25/01* (2006.01)
*A61B 90/00* (2016.01)

(52) U.S. Cl.
CPC ... *A61B 2090/376* (2016.02); *A61B 2090/378* (2016.02); *A61M 2025/0166* (2013.01)

(58) Field of Classification Search
CPC ........ A61B 2090/376; A61B 2090/378; A61B 2034/2046–2065
See application file for complete search history.

(56) References Cited

U.S. PATENT DOCUMENTS

| | | | |
|---|---|---|---|
| 5,395,353 A * | 3/1995 | Scribner | A61M 25/007 604/248 |
| 5,851,172 A | 12/1998 | Bueche et al. | |
| 6,115,630 A * | 9/2000 | Stadler | A61B 5/341 600/521 |
| 6,587,709 B2 | 7/2003 | Solf et al. | |
| 7,033,325 B1 | 4/2006 | Sullivan | |
| 7,403,811 B2 | 7/2008 | Sathanarayana | |
| 7,599,730 B2 * | 10/2009 | Hunter | A61B 1/00071 600/407 |
| 7,697,972 B2 * | 4/2010 | Verard | A61B 1/00071 600/407 |
| 7,769,427 B2 | 8/2010 | Shachar | |
| 7,873,402 B2 | 1/2011 | Shachar | |
| 7,887,549 B2 * | 2/2011 | Wenderow | A61B 34/30 606/108 |
| 9,545,497 B2 | 1/2017 | Wenderow et al. | |
| 2003/0097062 A1 | 5/2003 | Toth et al. | |
| 2003/0144590 A1 | 7/2003 | Maschke | |
| 2004/0097805 A1 | 5/2004 | Verard et al. | |
| 2004/0102697 A1 * | 5/2004 | Evron | A61B 6/5235 600/424 |
| 2004/0106916 A1 * | 6/2004 | Quaid | A61B 34/76 606/1 |
| 2005/0065434 A1 | 3/2005 | Bavaro et al. | |
| 2005/0256398 A1 | 11/2005 | Hastings et al. | |
| 2006/0015126 A1 | 1/2006 | Sher | |
| 2006/0241465 A1 | 10/2006 | Huennekens et al. | |
| 2006/0247521 A1 | 11/2006 | McGee | |
| 2007/0073271 A1 | 3/2007 | Brucker et al. | |
| 2007/0135709 A1 | 6/2007 | Rioux et al. | |
| 2008/0097187 A1 | 4/2008 | Gielen et al. | |
| 2008/0097195 A1 | 4/2008 | Urquhart et al. | |
| 2008/0123922 A1 | 5/2008 | Gielen et al. | |
| 2008/0262473 A1 | 10/2008 | Kornblau et al. | |
| 2009/0001276 A1 | 1/2009 | Yagi et al. | |
| 2009/0207965 A1 | 8/2009 | Sakaguchi | |
| 2009/0281418 A1 | 11/2009 | Ruijters et al. | |
| 2011/0137156 A1 | 6/2011 | Razzaque et al. | |
| 2011/0251483 A1 | 10/2011 | Razzaque et al. | |
| 2011/0319752 A1 | 12/2011 | Steinberg et al. | |
| 2012/0071751 A1 | 3/2012 | Sra et al. | |
| 2012/0071752 A1 | 3/2012 | Sewell et al. | |
| 2012/0071782 A1 | 3/2012 | Patil et al. | |
| 2012/0136242 A1 * | 5/2012 | Qi | A61B 5/349 600/424 |
| 2014/0187920 A1 | 7/2014 | Millett et al. | |
| 2015/0005620 A1 | 1/2015 | Bergman et al. | |
| 2015/0005738 A1 | 1/2015 | Blacker | |
| 2015/0005745 A1 | 1/2015 | Bergman et al. | |
| 2015/0005865 A1 | 1/2015 | Bergman et al. | |
| 2015/0164445 A1 | 6/2015 | Blau et al. | |

OTHER PUBLICATIONS

Ginapp, Todd; Ask the Clinical Instructor (A Q&A for those new to the cath lab); pp. 38-39; Cath Lab Digest; vol. 16—Issue 8; Aug. 2008; URL https://www.cathlabdigest.com/articles/Ask-Clinical-Instructor-11; 2 pages.

* cited by examiner

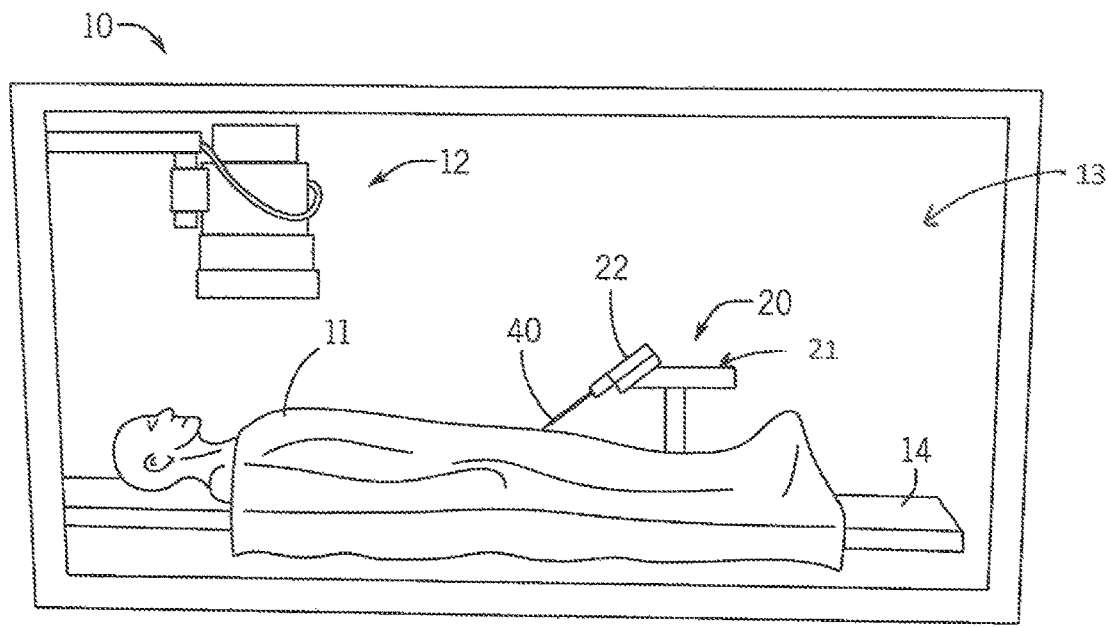
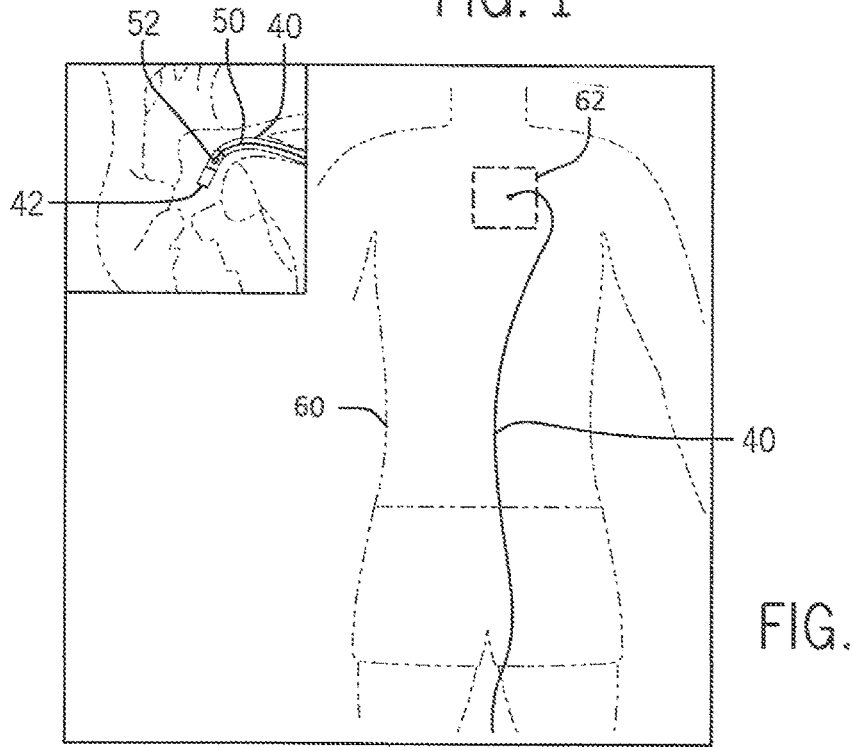
FIG. 1
FIG. 4

SYSTEM AND METHOD FOR MONITORING OF GUIDE CATHETER SEATING

CROSS REFERENCE TO RELATED APPLICATIONS

The present application claims the benefit of U.S. Provisional Application Ser. No. 61/864,808, filed Aug. 12, 2013 and U.S. Provisional Application Ser. No. 61/839,459, filed Jun. 26, 2013, both of which are herein incorporated by reference in their entirety.

FIELD OF THE INVENTION

The present invention relates generally to the field of catheter systems for performing diagnostic and/or therapeutic procedures and in particular, to a catheter procedure system and method configured to monitor and maintain the seating of a guide catheter.

BACKGROUND OF THE INVENTION

Systems exist for the robotic feeding of percutaneous interventional devices such as guide wires and working catheters into guide catheters. The guide catheters are typically placed by manual manipulation of medical personnel such that their distal ends are adjacent to the site of action for the intervention, typically a valve or chamber of the heart or a lesion in a blood vessel such as an artery. In the case of coronary arteries the guide catheter may be placed adjacent to the entrance of the artery into the aorta. The interventional devices such as guide wires and working catheters may be fed by the operation of robotic controls by medical personnel such as shown in U.S. Pat. No. 7,887,549 and U.S. Published Application No. 2012/0179032. It is desirable that the guide catheter remain in place while a guide wire or a working catheter is passed through it and to the site of action, particularly when the distal end of the guide catheter has been in the ascending aorta with the distal end of its lumen coaxial with the ostium of the coronary artery giving access to the site of action such as a lesion. However, there is also a tendency for a guide catheter to move in a proximal direction as a guide wire or a working catheter is moved through it in a distal direction.

It would be desirable to provide a system and method for monitoring the seating of a guide catheter during a catheter procedure and to automatically adjust the position of the guide catheter if the guide catheter is out of position.

SUMMARY OF THE INVENTION

In accordance with an embodiment, a method for monitoring the seating of a guide catheter during a catheter procedure includes monitoring at least one parameter of the catheter procedure, determining if the at least one parameter indicates that a guide catheter is out of position, displaying an alert if the at least one parameter indicates the guide catheter is out of position and adjusting the position of the guide catheter automatically using a robotic catheter system.

In accordance with another embodiment, a catheter procedure system includes a bedside system comprising a guide catheter and a guide catheter drive mechanism coupled to the guide catheter, and a workstation coupled to the bed side system, the workstation including a user interface, at least one display, a controller coupled to the bedside system, the user interface, and the at least one display, the controller programmed to monitor at least one parameter of the catheter procedure, determine if the at least one parameter indicates that the guide catheter is out of position, display an alert on the at least one display if the at least one parameter indicates the guide catheter is out of position, and adjust the position of the guide catheter by controlling the guide catheter drive mechanism.

In accordance with another embodiment, a non-transitory computer readable storage medium having computer executable instructions for performing a method for monitoring the seating of a guide catheter during a catheter procedure includes program code for monitoring at least one parameter of the catheter procedure, program code for determining if the at least one parameter indicates that the guide catheter is out of position, program code for displaying an alert if the at least one parameter indicates the guide catheter is out of position and program code for adjusting the position of the guide catheter automatically using a robotic catheter system.

BRIEF DESCRIPTION OF THE DRAWINGS

This application will become more fully understood from the following detailed description, taken in conjunction with the accompanying figures, wherein like reference numerals refer to like elements in which:

FIG. 1 is a perspective view of an exemplary catheter procedure system in accordance with an embodiment;

FIG. 4 is a schematic of the placement of a guide catheter and a guide wire in a human body in accordance with an embodiment.

DETAILED DESCRIPTION OF THE PREFERRED EMBODIMENTS

Figure 2:
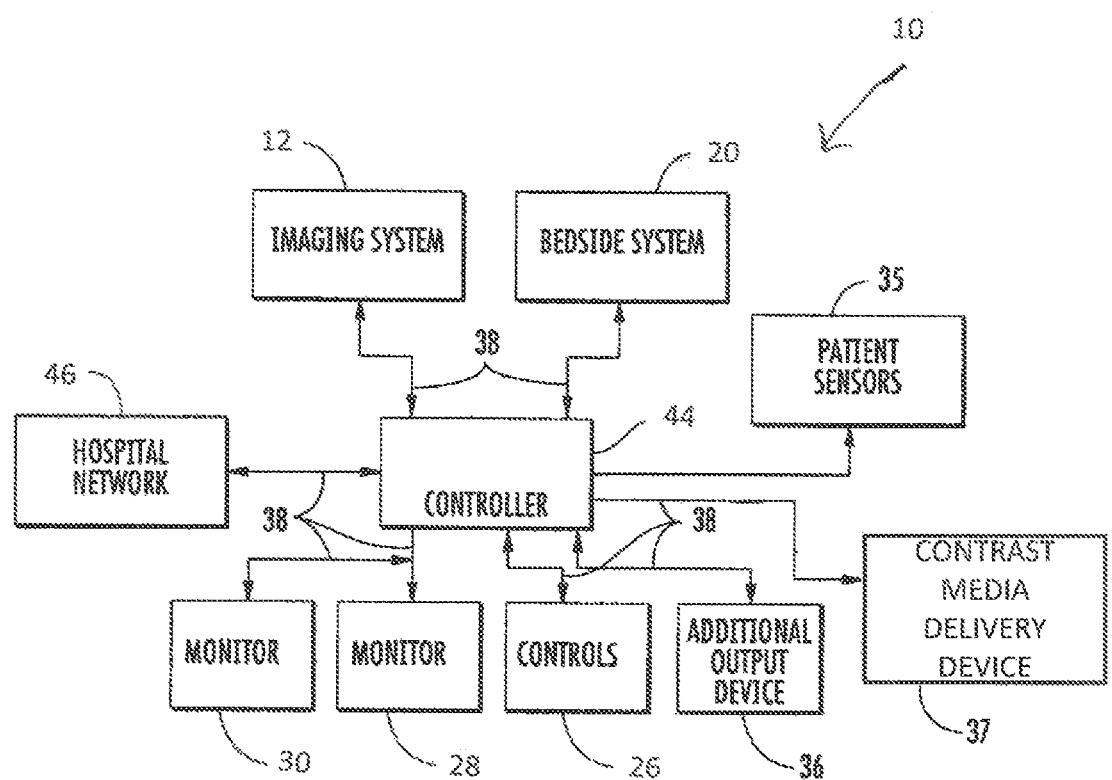
FIG. 2 is a schematic block diagram of a catheter procedure system in accordance with an embodiment.

FIG. 1 is a perspective view of an exemplary catheter procedure system in accordance with an embodiment. In FIG. 1, a catheter procedure system 10 may be used to perform catheter based medical procedures (e.g., percutaneous intervention procedure). Percutaneous intervention procedures may include diagnostic catheterization procedures during which one or more catheters are used to aid in the diagnosis of a patient's disease. For example, during one embodiment of a catheter based diagnostic procedure, a contrast media is injected onto one or more coronary arteries through a catheter and an image of the patient's heart is taken. Percutaneous intervention procedures may also include catheter based therapeutic procedures (e.g., angioplasty, stent placement, treatment of peripheral vascular disease, etc.) during which a catheter is used to treat a disease. It should be noted, however, that one skilled in the art would recognize that certain specific percutaneous intervention devices or components (e.g., type of guide wire, type of catheter, etc.) will be selected based on the type of procedure that is to be performed. Catheter procedure system 10 is capable of performing any number of catheter based medical procedures with minor adjustments to accommodate the specific percutaneous intervention devices to be used in the procedure. In particular, while the embodiments of catheter procedure system 10 describe herein are explained primarily in relation to the diagnosis and/or treatment of coronary disease, catheter procedure system 10 may be used to diagnose and/or treat any type of disease or condition amenable to diagnosis and/or treatment via a catheter based procedure.

Catheter procedure system 10 also includes lab unit 13 and workstation 24. Catheter procedure system 10 includes a robotic catheter system, shown as bedside system 20, located within lab unit 13 adjacent a patient 11. Patient 11 is supported on a table 14. Generally, bedside system 20 may be equipped with the appropriate percutaneous intervention devices or other components (e.g., guide wires, guide catheters, working catheters, catheter balloons, stents, contrast media, medicine, diagnostic catheters, etc.) to allow the user to perform a catheter based medical procedure via a robotic system by operating various controls such as the controls located at workstation 24. Bedside system 20 may include any number and/or combination of components to provide bedside system 20 with the functionality described herein. Bedside system 20 includes, among other elements, a cassette 22 supported by a robotic arm 21 which is used to automatically feed a guide wire 50 (shown in FIG. 4) into a guide catheter 40 seated in an artery of the patient 11. Various embodiments of bedside system 20 are described in detail in International Application No. PCT/US2009/042720, filed May 4, 2009 and U.S. Pat. No. 7,887,549, both of which are incorporated herein by reference in their entirety.

Bedside system 20 is in communication with workstation 24, allowing signals generated by the user inputs of workstation 24 to be transmitted to bedside system 20 to control the various functions of bedside system 20. Bedside system 20 may also provide feedback signals (e.g., operating conditions, warning signals, error codes, etc.) to workstation 24. Bedside system 20 may be connected to workstation 24 via a communication link 38 (shown in FIG. 2) that may be a wireless connection, cable connections, or any other means capable of allowing communication to occur between workstation 24 and bedside system 20.

Workstation 20 is capable of being remotely located, for example, in either a procedure room or a separate control room. Workstation 24 may be located at any place within a hospital. Workstation 24 may also be in any location outside of the hospital, such as in a physician's offsite office, mobile workstation trailer, etc. If workstation 24 is located such that the user is not able to directly view patient 11 within lab unit 13, lab unit 13 may be equipped with a camera to allow the user located at workstation 24 to see the patient within lab unit 13. If imaging system 12 is a radiation based imaging device, remotely locating workstation 24 enables users to perform procedures outside the radiation zone created by imaging system 12. In addition, remotely locating workstation 24 may allow users to multitask outside the procedure room during downtime.

Workstation 24 includes a user interface 34. User interface 34 includes controls 26 that allow the user to control bedside system 20 to perform a catheter based medical procedure. For example, controls 26 may be configured to cause bedside system 20 to perform various tasks using the various percutaneous intervention devices with which bedside system 20 may be equipped (e.g., to advance, retract, or rotate a guide wire, advance, retract or rotate a working catheter, advance, retract, or rotate a guide catheter, inflate or deflate a balloon located on a catheter, position and/or deploy a stent, inject contrast media into a catheter, inject medicine into a catheter, or to perform any other function that may be performed as part of a catheter based medical procedure). Cassette 22 includes various drive mechanisms to cause movement (e.g., axial and rotational movement) of the components of the bedside system 20 including the percutaneous intervention devices.

In one embodiment, controls 26 include a touch screen 32, one or more joysticks 70 and buttons 72, 74. The joystick 70 may be configured to advance, retract, or rotate various components and percutaneous intervention devices such as, for example, a guide wire, a guide catheter or a working catheter. Buttons 72, 74 may include, for example, an emergency stop button and a multiplier button. When an emergency stop button is pushed a relay is triggered to cut the power supply to bedside system 20. Multiplier button acts to increase or decrease the speed at which the associated component is moved in response to a manipulation of controls 26. In one embodiment, controls 26 may include one or more controls or icons (not shown) displayed on touch screen 32, that, when activated, causes operation of a component of the catheter procedure system 10. Controls 26 may also include a balloon or stent control that is configured to inflate or deflate a balloon and/or a stent. Each of the controls may include one or more buttons, joysticks, touch screen, etc. that may be desirable to control the particular component to which the control is dedicated. In addition, touch screen 32 may display one or more icons (not shown) related to various portions of controls 26 or to various components of catheter procedure system 10.

User interface 34 may include a first monitor or display 28 and a second monitor or display 30. First monitor 28 and second monitor 30 may be configured to display information or patient specific data to the user located at workstation 24. For example, first monitor 28 and second monitor 30 may be configured to display image data (e.g., x-ray images, MRI images, CT images, ultrasound images, etc.), hemodynamic data (e.g., blood pressure, heart rate, etc.), patient record information (e.g., medical history, age, weight, etc.). In addition, first monitor 28 and second monitor 30 may be configured to display procedure specific information (e.g., duration of procedure, catheter or guide wire position, volume of medicine or contrast agent delivered, etc.). Monitor 28 and monitor 30 may be configured to display information regarding the position the guide catheter. Further, monitor 28 and monitor 30 may be configured to display information to provide the functionalities associated with controller 44 (shown in FIG. 2) discussed below. In another embodiment, user interface 34 includes a single screen of sufficient size to display one or more of the display components and/or touch screen components discussed herein.

Catheter procedure system 10 also includes an imaging system 12 located within lab unit 13. Imaging system 12 may be any medical imaging system that may be used in conjunction with a catheter based medical procedure (e.g., non-digital x-ray, digital x-ray, CT, MRI, ultrasound, etc.). In an exemplary embodiment, imaging system 12 is a digital x-ray imaging device that is in communication with workstation 24. In one embodiment, imaging system 12 may include a C-arm (not shown) that allows imaging system 12 to partially or completely rotate around patient 11 in order to obtain images at different angular positions relative to patient 11 (e.g., sagittal views, caudal views, anterior-posterior views, etc.).

Imaging system 12 may be configured to take x-ray images of the appropriate area of patient 21 during a particular procedure. For example, imaging system 12 may be configured to take one or more x-ray images of the heart to diagnose a heart condition. Imaging system 12 may also be configured to take one or more x-ray images during a catheter based medical procedure (e.g., real time images) to assist the user of workstation 24 to properly position a guide wire, guide catheter, stent, etc. during the procedure. The image or images may be displayed on first monitor 28 and/or second monitor 30. In particular, images may be displayed on first monitor 28 and/or second monitor 30 to allow the user to, for example, accurately move a guide catheter into the proper position.

In addition, a user of workstation 24 may be able to control the angular position of imaging system 12 relative to the patient to obtain and display various views of the patient's heart on first monitor 28 and/or second monitor 30. Displaying different views at different portions of the procedure may aid the user of workstation 24 to properly move and position the percutaneous intervention devices within the 3D geometry of the patient's heart. In an embodiment, imaging system 12 may be any 3D imaging modality such as an x-ray based computed tomography (CT) imaging device, a magnetic resonance imaging device, a 3D ultrasound imaging device, etc. In this embodiment, the image of the patient's heart that is displayed during the procedure may be a 3D image. In addition, controls 26 may also be configured to allow the user positioned at workstation 24 to control various functions of imaging system 32 (e.g., image capture, magnification, collimation, c-arm positioning, etc.).

Referring to FIG. 2, a block diagram of catheter procedure system 10 is shown according to an exemplary embodiment. Catheter procedure system 10 may include a control system, shown as controller 44. Controller 44 may be part of workstation 24. Controller 44 is in communication with one or more bedside systems 20, controls 26, monitors 28 and 30, imaging system 12 and patient sensors 35 (e.g., electrocardiogram ("ECG") devices, electroencephalogram ("EEG") devices, blood pressure monitors, temperature monitors, heart rate monitors, respiratory monitors, etc.). In addition, controller 44 may be in communication with a hospital data management system or hospital network 46, one or more additional output devices 36 (e.g., printer, disk drive, cd/dvd writer, etc.) and a contrast media delivery device 37. The contrast media delivery device 37 may be any device configured to allow a user to administer contrast agent or dye to patient 11 during the catheter procedure. Contrast media delivery device 37 may be connected (e.g., using a conduit) to one or more percutaneous intervention devices of the catheter procedure system such as a guide catheter. Contrast media delivery device 37 may include various components, for example, pumps, valves, power supplies, contrast media reservoirs, etc.

Communication between the various components of catheter procedure system 10 may be accomplished via communication links 38. Communication links 38 may be dedicated wires or wireless connections. Communication links 38 may also represent communication over a network. Catheter procedure system 10 may be connected or configured to include any other systems and/or devices not explicitly shown. For example, catheter procedure system 10 may include IVUS systems, image processing engines, data storage and archive systems, automatic balloon and/or stent inflation systems, medicine injection systems, medicine tracking and/or logging systems, user logs, encryption systems, systems to restrict access or use of catheter procedure system 10, etc.

Figure 3:
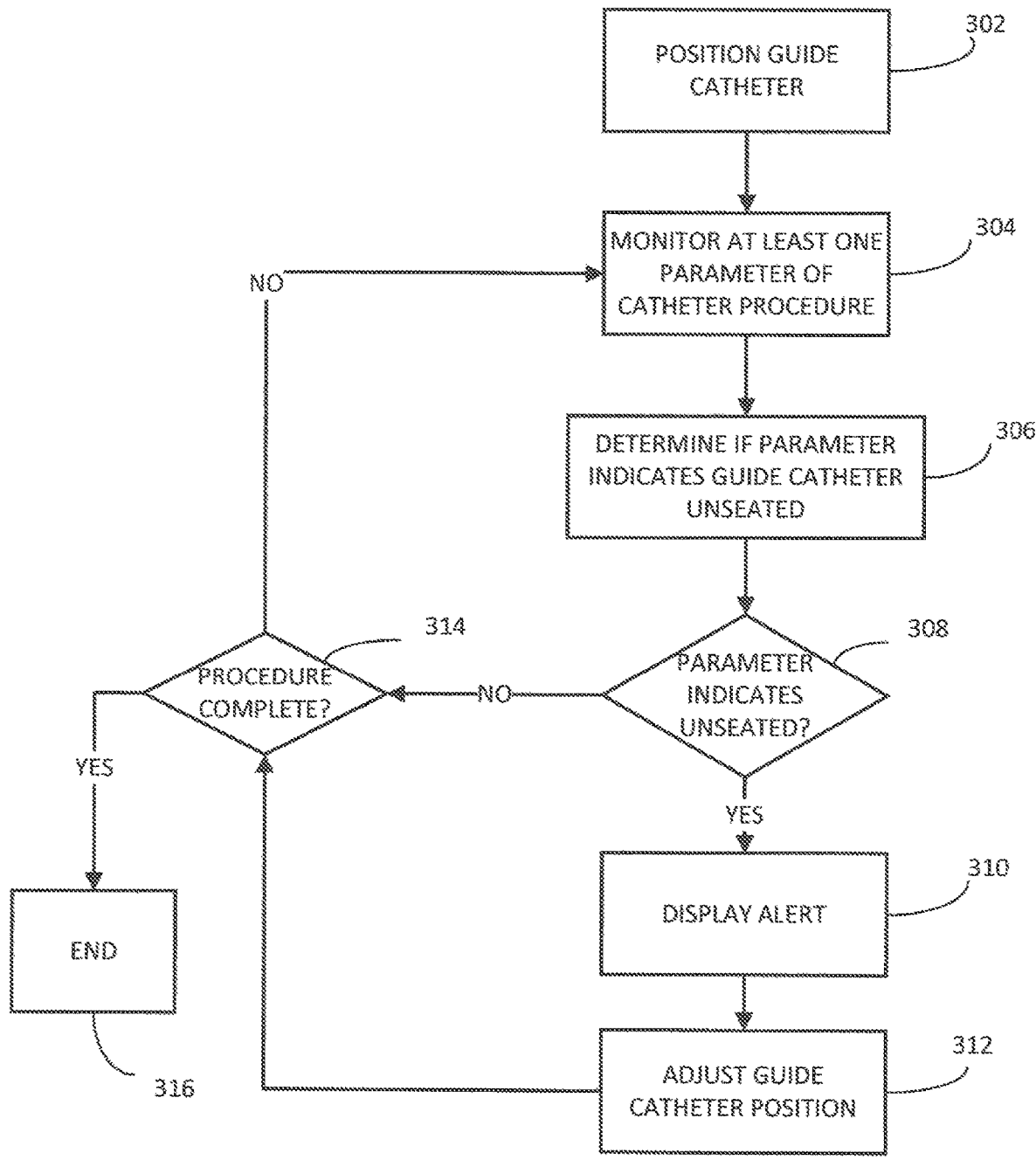
FIG. 3 illustrates a method of monitoring guide catheter seating in accordance with an embodiment.
Figure 5:
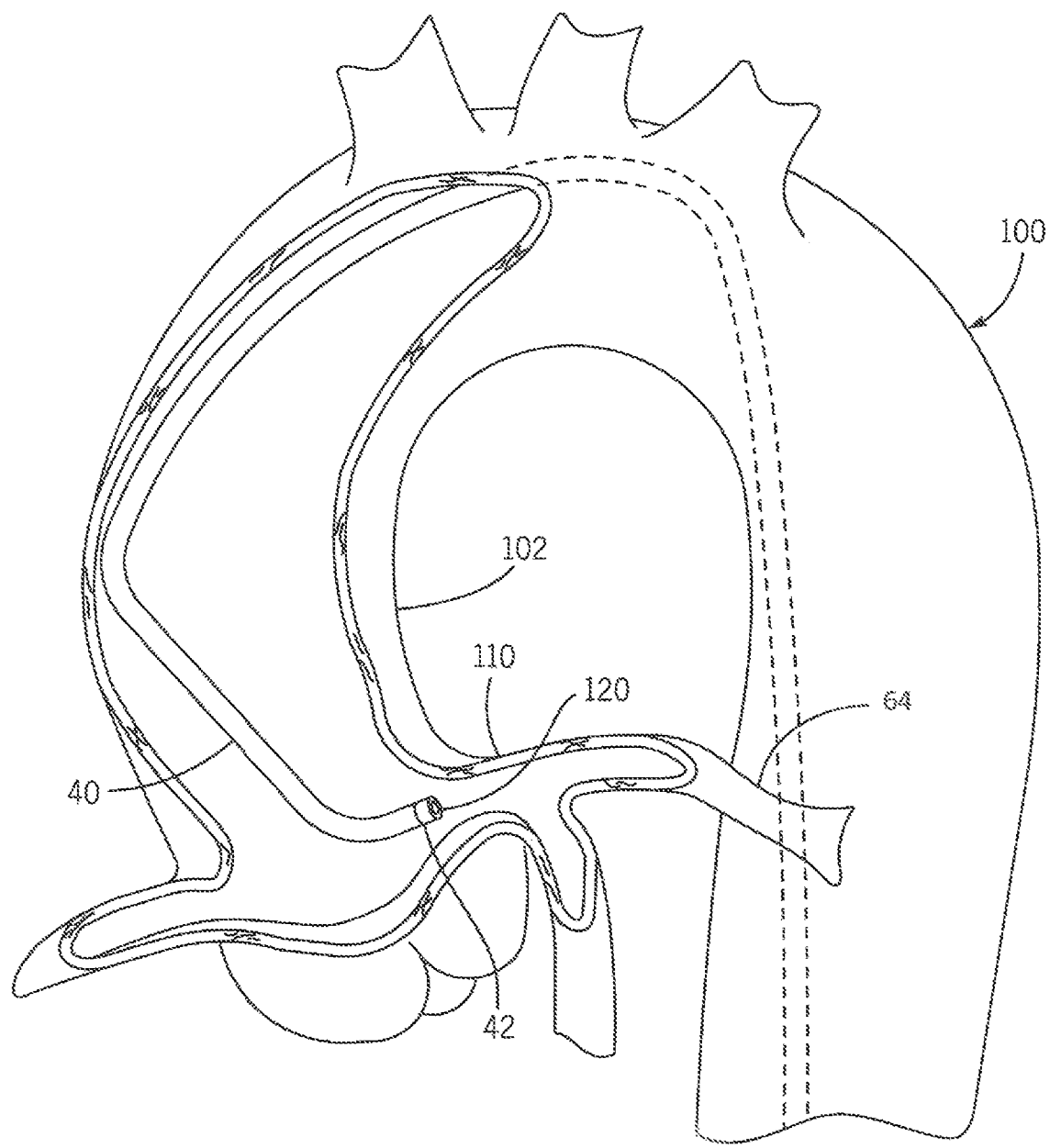
FIG. 5 a schematic of a guide catheter properly seated in the ostium of the Left Coronary Artery (LCA) in accordance with an embodiment.

FIG. 3 illustrates a method of monitoring guide catheter seating in accordance with an embodiment. At block 302, a catheter procedure system, such as catheter procedure system 10 shown in FIG. 1, is used to position a guide catheter in a patient for a catheter procedure. FIG. 4 is a schematic of placement of a guide catheter and a guide wire in a human body in accordance with an embodiment. In FIG. 4, a guide catheter 40 has been fed into the torso 60 of a patient 11 to reach the cardiac region 62. Within the guide catheter 40 is a guide wire 50 whose tip 52 has not yet passed out of the distal end 42 of the guide catheter 40. An imaging system, for example, an x-ray system, may be used to monitor the progress of the guide catheter 40 and the guide wire 50 as it passes through the guide catheter 40. FIG. 5 is a schematic of a guide catheter properly seated in the ostium of the Left Coronary Artery (LCA) in accordance with an embodiment. In FIG. 5, a guide catheter 40 has been fed through the aorta 100 and seated in the ascending aorta 102 with its distal end 42 is properly positioned in the ostium of the left coronary artery 110 with the distal end 120 of the lumen of the guide catheter coaxial with the left coronary artery 110. The guide catheter 40 is now in position to support the delivery of a guide wire 50 to a downstream coronary artery 60 which is in need of a therapeutic intervention to address a concern such as a lesion. In other embodiments, certain catheter procedures may require the distal end of the guide catheter to be deeply seated in a coronary artery.

Returning to FIG. 3, at block 304, at least one parameter of the catheter procedure is monitored by the catheter procedure system 10 (shown in FIGS. 1 and 2). Controller 44 (shown in FIG. 2) may be configured to monitor the parameter or parameters. The at least one parameter is monitored during the catheter procedure by controller 44 to determine, at block 306, if the parameter indicates that the guide catheter is unseated (i.e., is out of position or non-coaxial) from its fully deployed position. Changes in the various parameters of the catheter procedure indicate that a guide catheter has become unseated. The determination of whether the guide catheter is unseated can be based on one parameter or a combination of multiple parameters. Parameters that may be monitored include, but are not limited to, blood pressure, electrocardiogram waveforms or signals, contrast agent, fluoroscopic images of a region including the distal end of the guide catheter and ultrasound signals. In one embodiment, a predetermined threshold may be set that indicates that a guide catheter has become unseated from its fully deployed position. Controller 44 may then monitor the parameter to determine if it has exceeded or fallen below the predetermined threshold. For example, the normal range of variance of the monitored parameter may be determined and a threshold set so that if the parameter moves out of that range in a particular direction it is correlated with the guide catheter becoming unseated.

In one embodiment, the parameter that is monitored by the controller 44 may be blood pressure, for example, the arterial blood pressure in a blood vessel involved in the catheter procedure. As mentioned above, controller 44 may be coupled to patient sensors 35 such as a blood pressure sensor or monitor. In one embodiment, the blood pressure sensor may be coupled to the end of the guide catheter proximate to the bedside system, for example, through a manifold and the sensor measures the blood pressure at the distal end of the guide catheter. Various characteristics of blood pressure waveforms, such as damping and ventricularization, are indicative that the distal end of a guide catheter is no longer properly positioned (e.g., seated too deeply or tipped up against the wall of an artery). Damping is evidenced by decreasing systolic pressure and may be an indication that the tip of the distal end of the guide catheter is in contact with a wall of the aorta or the coronary artery being addressed by the guide catheter or may be an indication that there is a mismatch between the guide catheter and the ostium of the vessel. Ventricularization is evidenced by a slight decrease in systolic pressure and a large decrease in diastolic pressure and may be an indication that the guide catheter has occluded a coronary artery. The occlusion may be caused, for example, by the distal end of the guide catheter encountering a lesion such that blood flow around the guide catheter is no longer possible.

In another embodiment, the parameter monitored by the controller 44 may be an electrocardiogram waveform or signal such as the ST waveform or segment. As mentioned above, the controller 44 may be coupled to patient sensors 35 such as electrocardiogram ("ECG") devices. The ST segment connects the QRS complex and the T wave of the electrocardiogram. Elevation of the ST waveform (or "ST elevation") is an indication of a blockage in the vessel or myocardial infarction which may be caused by the guide catheter being seated too deeply in the coronary artery or positioned such that it blocks blood flow. ST elevation refers to a finding on the electrocardiogram that the trace in the ST segment is abnormally high above the isoelectric line.

In another embodiment, the parameter monitored by the controller 44 may be the flow path of a contrast agent. As mentioned, the catheter procedure system 10 may include a contrast media delivery device 37 that may be coupled to the controller 44. Appearance of contrast agent or dye outside of the target blood vessel for the catheter procedure may indicate that the guide catheter is unseated. For example, in the case of coronary arteries the guide catheter may be seated with the distal end of its lumen adjacent to and coaxial with the entrance to a coronary artery that is being used to access one of the coronary arties that branches off this artery further downstream. In such a case the access artery may be considered the target blood vessel and the appearance of contrast agent or dye in the ascending aorta may be the indication of unseating of the guide catheter. In one embodiment, controller 44 is configured to process images (e.g. acquired using the imaging system) of the region of interest for the catheter procedure to detect when more than a preset amount of dye or contrast agent is observed in an inappropriate place. For example, a contrast media delivery device 37 of the catheter procedure system may be used to deliver contrast agent to the distal end of the guide catheter so that the contrast agent is expelled from the distal end of the guide catheter and the flow path of the contrast agent may be observed with fluoroscopic imaging. In one embodiment, the image processing may include comparing two registered images by subtracting from each other and thresholding the resulting subtracted image and comparing the size of the threshold area. The two registered images may be comprised of a reference image and a current image or the two registered images may be comprised of two successive images, In another embodiment, the controller 44 may be configured to monitor and compare images of the region of interest to determine if the distal end of the guide catheter is out of position. In one embodiment, the images are fluoroscopic x-ray images. In one embodiment, the image processing may include comparing images to identify if the position of the distal end of the guide catheter has changed. For example, when a working catheter is moved through the guide catheter, the guide catheter may move in an axial direction away from the ostium. The images being compared may be comprised of a reference image (or a roadmap image) and a current image (or images) or the images being compared may be comprised of two successive images. In another embodiment, an ultrasound imaging system may be used to determine if the position of the distal end of the guide catheter has changed and that the guide catheter is out of position. For example, ultrasound waves may be sent along the guide catheter and the position of the distal end of the guide catheter may be determined based on the return signals received be the ultrasound imaging system.

At block 308, if the parameter (or parameters) indicates that the guide catheter is unseated, an alert is displayed at block 310. For example, controller 44 may be configured to generate an alert on display 28 and/or display 30 of the catheter procedure system 10. Alternatively, the alert may be an audible signal. Controller 44 may more quickly and reliably provide an alarm then medical personnel observing the procedure depending on how the thresholds are set.

At block 312, the position of the guide catheter is adjusted to return the guide catheter to a properly seated position. In one embodiment, controller 44 may be configured to automatically adjust the position of the guide catheter using the bedside system. For example, the guide catheter may be adjusted in an axial direction (i.e., advance or retract) or the guide catheter may be rotated. Automatic adjustment may be particularly helpful when the guide catheter is moved out of position by small movements made by a user to advance a guide wire or working catheter through the guide catheter or when the guide catheter is moved out of position in response to physiological causes such as the cardiac cycle. One of the benefits of automatic adjustment of the position of a guide catheter is that it may be rapid enough that the need for manual intervention by the involved medical personnel may not become necessary. At block 314, if the catheter procedure is complete, the process ends at block 316. If the catheter procedure is not complete, the process returns to block 304 and the system monitors at least one parameter of the catheter procedure system. In one embodiment, if the position of the guide catheter was adjusted in response to a change in a parameter, the controller 44 may monitor the system parameters to confirm that the catheter is reseated in the proper position. For example, the controller 44 may be configured to monitor and determine if the parameter has returned to a normal range after an adjustment of the guide catheter position.

At block 308, if the parameter does not indicate that the guide catheter is unseated, the process moves to block 314. If the catheter procedure is complete at block 314, the process ends at block 316. If the catheter procedure is not complete, the process returns to block 304 and the system monitors at least one parameter of the catheter procedure system.

Computer-executable instructions for monitoring and maintaining guide catheter seating according to the above-described method may be stored on a form of computer readable media. Computer readable media includes volatile and nonvolatile, removable, and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital versatile disks (DVD) or other optical storage, magnetic cassettes, magnetic tape, magnetic disk storage or other magnetic storage devices, or any other medium which can be used to store the desired instructions and which may be accessed by system 10 (shown in FIG. 1), including by internet or other computer network form of access.

This written description used examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims. The order and sequence of any process or method steps may be varied or re-sequenced according to alternative embodiments.

Many other changes and modifications may be made to the present invention without departing from the spirit thereof. The scope of these and other changes will become apparent from the appended claims.

What is claimed is:

1. A method for maintaining the position of a catheter during a catheter based medical procedure; the method comprising:
    positioning a distal end of a catheter in a position to support delivery of a device to a location downstream of the position relative to a feeding direction of the catheter to perform the catheter based medical procedure;
    while the catheter based medical procedure is being performed, automatically monitoring, using a controller, an ST waveform of an electrocardiogram;
    while the catheter based medical procedure is being performed, automatically determining, using the controller, that the monitored ST waveform is elevated;
    in response to determining that the monitored ST waveform is elevated, automatically determining, using the controller, that the distal end of the catheter has moved from the position;
    and
    while the catheter based medical procedure is being performed, and in response to determining that the distal end of the catheter has moved from the position, automatically adjusting the catheter using a robotic catheter system to return the distal end of the catheter to the position.

2. A method according to claim 1, wherein automatically determining that the monitored ST waveform is elevated comprises automatically determining that the monitored ST waveform is abnormally high above an isoelectric line.

3. The method of claim 1, wherein the robotic catheter system further includes a second drive mechanism to robotically drive the device through the catheter.

4. The method of claim 3, wherein the device is one of a guide wire, working catheter, catheter balloon, and stent.

5. The method of claim 3, wherein the position is in an ostium of a left coronary artery with a distal end of a lumen of the catheter being coaxial with the left coronary artery.

6. A method for monitoring the position of a catheter during a catheter based medical procedure; the method comprising:
    positioning a distal end of a catheter in a position to support delivery of a device to a location downstream of the position relative to a feeding direction of the catheter to perform the catheter based medical procedure;
    while the catheter based medical procedure is being performed, automatically monitoring, using a controller, an ST waveform of an electrocardiogram;
    while the catheter based medical procedure is being performed, automatically determining, using the controller, that the monitored ST waveform is elevated;
    in response to determining that the monitored ST waveform is elevated, automatically determining, using the controller, that the distal end of the catheter is not in the position;
    and
    while the catheter based medical procedure is being performed, and in response to determining that the monitored ST waveform indicates that the distal end of the catheter is not in the position, automatically adjusting the catheter using a robotic catheter system to return the distal end of the catheter to the position,
    wherein the robotic catheter system includes a bedside system having a drive mechanism to perform the catheter based medical procedure using the controller.

7. A method according to claim 6, wherein automatically determining that the ST waveform is elevated comprises automatically determining that the ST waveform is abnormally high above an isoelectric line.

8. A method according to claim 6, wherein the location is a target blood vessel.

9. A catheter procedure system comprising:
    a robotic catheter system including a bedside system to perform a catheter based medical procedure, the bedside system comprising:
    a catheter having a distal end positioned at a position to support delivery of a device to a location downstream of the position relative to a feeding direction of the catheter to perform the catheter based medical procedure; and
    a catheter drive mechanism coupled to the catheter; and a workstation coupled to the bedside system, the workstation comprising:
    a user interface;
    at least one display;
    a controller coupled to the bedside system, the user interface, and the at least one display, the controller programmed to:
    while the catheter based medical procedure is being performed, automatically monitor an ST waveform of an electrocardiogram;
    while the catheter based medical procedure being performed, automatically determine that the monitored ST waveform is elevated;
    in response to determining that the monitored ST waveform is elevated, automatically determine that the distal end of the catheter has moved from the position;
    and
    while the catheter based medical procedure is being performed, and in response to determining that the monitored ST waveform indicates that the distal end of the catheter has moved from the position, automatically adjust the catheter by controlling the catheter drive mechanism to return the distal end of the catheter to the position.

10. A system according to claim 9, wherein automatically determining that the ST waveform is elevated comprises automatically determining that the ST waveform is abnormally high above an isoelectric line.

11. A catheter procedure system comprising:
    a robotic catheter system including a bedside system to perform a catheter based medical procedure, the bedside system comprising:
    a catheter having a distal end positioned at a position to support delivery of a device to a location downstream of the position relative to a feeding direction of the catheter to perform the catheter based medical procedure; and a catheter drive mechanism coupled to the catheter; and a workstation coupled to the bedside system, the workstation comprising:

a user interface;

at least one display;

a controller coupled to the bedside system, the user interface, and the at least one display, the controller programmed to:

while the catheter based medical procedure is being performed, automatically monitor an ST waveform of an electrocardiogram;

while the catheter based medical procedure being performed, automatically determine that the monitored ST waveform is elevated;

in response to determining that the monitored ST waveform is elevated, automatically determine that the distal end of the catheter is not in the position; and while the catheter based medical procedure is being performed, and in response to determining that the end of the catheter is not in the position, automatically adjust the catheter by controlling the catheter drive mechanism to return the distal end of the catheter to the position.

12. A method according to claim 11, wherein automatically determining that the ST waveform is elevated comprises automatically determining that the ST waveform is abnormally high above an isoelectric line.

13. A non-transitory computer readable storage medium having computer executable instructions for performing a method for maintaining the position of a catheter during a catheter based medical procedure, the computer readable storage medium comprising:

program code executable by a controller for automatically monitoring an ST waveform of an electrocardiogram while the catheter based medical procedure is being performed, wherein the catheter based medical procedure includes positioning with a robotic catheter system a distal end of a catheter in a position to support delivery of a device to a location downstream of the position relative to a feeding direction of the catheter to perform the catheter based medical procedure;

program code executable by the controller for automatically determining that the monitored ST waveform is elevated while the catheter based medical procedure is being performed;

program code executable by the controller for automatically determining, in response to the determination that the monitored ST waveform is elevated, that the distal end of the catheter has moved from the position; and program code executable by the controller for automatically adjusting the position of the catheter automatically using a robotic catheter system to return the distal end of the catheter to the position.

14. A non-transitory computer readable storage medium according to claim 13, wherein automatically determining that the ST waveform of the electrocardiogram is elevated comprises automatically determining that the ST waveform is abnormally high above an isoelectric line.

\* \* \* \* \*